United States Patent [19]

Danielson

[11] Plant 4,001

[45] Jan. 4, 1977

[54] CHRYSANTHEMUM PLANT NAMED IMPROVED YELLOW DIGNITY

[75] Inventor: Robert E. Danielson, West Chicago, Ill.

[73] Assignee: Pan American Plant Company, West Chicago, Ill.

[21] Appl. No.: 605,557

[22] Filed: Aug. 18, 1975

[51] Int. Cl.[2] ..... A01H 5/00

[52] U.S. Cl. ..... Plt./78

[58] Field of Search ..... Plt./78

*Primary Examiner*—Robert E. Bagwill

*Attorney, Agent, or Firm*—Charles W. Rummler

[57] ABSTRACT

A new and distinct variety of chrysanthemum plant of the standard incurved type for greenhouse culture which originated as an irradiated mutation of "Yellow Dignity" (P.P. 3587) and which is distinguished from the cultivar by the more intense yellow color of its blooms.

2 Drawing Figures

BACKGROUND OF THE INVENTION

This new variety of chrysanthemum plant is the result of my efforts to produce improved chrysanthemum varieties for the commercial market and was discovered by me in 1972 at West Chicago, Ill., among a group of mutations which resulted from irradiation of plants of the variety "Yellow Dignity" (U.S. Plant Pat. No. 3,587). This particular plant was selected for propagation and trial because of its brighter yellow color than that of its parent. Asexual propagation of this new plant was carried on by me and under my direction at West Chicago, Ill., by means of cuttings from the original plant, as well as cuttings from rooted scions of the original plant, and in all cases, the resulting plants have clearly demonstrated that the distinguishing characteristics of the new variety hold true from generation to generation and are firmly fixed. Propagation of this new variety is now carried on by means of vegetative cuttings at West Chicago, Ill., and at Cortez, Fla., and the distinguishing characteristics of this variety grown at both regions appear to hold true.

DESCRIPTION OF THE DRAWINGS

This new variety of chrysanthemum plant is illustrated by the accompanying drawings, of which:

Sheet 1 shows the color characteristics of the flowers in two views as nearly true as it is reasonably possible to obtain by conventional photographic procedures, one view showing the face of a fully opened bloom and the other showing a blooming stem and foliage; and Sheet 2 shows, in face and side views, a color comparison of the flowers of the parent plant and the improved variety, the parent plant flower being at the left in each view and the two views showing the general color effect as it actually appears when the flowers are viewed from a distance of 6 to 10 feet.

DESCRIPTION OF THE NEW PLANT

The following is a detailed description of my new variety of chrysanthemum plant with color designations according to the RHS Colour Chart and the Horticultural Colour Chart (HCC) published by the Royal Horticultural Society of London, England.

THE PLANT

Origin: Irradiated mutation.

Parentage: "Yellow Dignity", U.S. Plant Pat. No. 3,587, a sport originated by irradiation of the variety "Dignity", U.S. Plant Pat. No. 3,309.

Classification:

*Botanic.*—*Chrysanthemum morifolium.*

*Commercial.*—Greenhouse standard incurved.

Form: Perennial herbaceous bush.

Height: 2½ to 3½ feet.

Growth: Terminal. Very vigorous, upright and with good strength.

Branching: Normal for this type of chrysanthemum plant.

Foliage: Abundant with about 11 leaves per foot of upper stem length.

*Leaf Size.*—Mature leaf—5½ to 7½ inches long and 3½ to 4½ inches wide.

*Shape.*—Lobed—lanceolate.

*Surface Texture.*—Glaucescent.

*Color.*—Upper side—Green Group 137A. Under side—Green Group 137B and 147B.

*Venation.*—Pinnately veined.

*Petioles.*—Length—1⅛ to 1½ inches.

THE BUD

Form: Generally globular, oval from a side view.

Size: Large. ⅝ inch to 1⅛ inch in diameter and ⅜ to ⅞ inch in depth as phyllaries begin to open.

Opening Rate: Bud opens slowly. Phyllaries begin to divide about two weeks after bud becomes visible and flowering occurs about 25 days later.

Color:

*When phyllaries first divide.*—Yellow Group 3C.

*When florets begin to unfurl.*—Yellow Group 6A.

Phyllaries: The outside of the receptacle bears many involucral bracts which are distinct, spear-shaped and stand up.

*Color.*—Inside—Green Group 137A to C. Outside—Green Group 137A to C.

*Surface Aspect.*—Canescent.

Calyx: The calyx is represented by tiny bristles arising from the top of the ovary. Occasionally the calyx may be absent.

Peduncle: Length—2½ to 5 inches depending upon culture and growing season.

*Strength.*—Strong and erect.

*Surface Aspect.*—Canescent.

THE FLOWER

Blooming Period: With photoperiod control, this variety can be flowered the year around.

Response: 9 weeks

Natural Season Flowering: Late October to early November.

Recommended Flowering: April through November.

Blooms: Flower type—incurved.

*Borne.*—A head of many florets borne on a receptacle.

*Size.*—Very large. Diameter—5 to 6½ inches. Depth—3½ to 5 inches.

*Shape.*—Rather flat when bloom first opens, becoming more globular as the flower matures.

Florets: Many, in capitulum arrangement.

*Form.*—Linear and somewhat incurved with longitudinal petal roll and an apex varying from acute to obtuse.

*Color.*—

| | Summer | Winter |
|---|---|---|
| Outer Florets: | | |
| Top side | Yel. Group 4B | Yel. Group 6B |
| Reverse side | Yel. Group 4C | Yel. Group 6C |
| Inner Florets: | | |
| Top side | Yel. Group 5A | Yel. Group 6A |
| Reverse side | Yel. Group 5B | Yel. Group 6B |

*Firmness.*—Medium.

*Appearance.*—Velvety.

Peduncle: Length—2½ to 5 inches depending upon culture and season of growth.

*Color.*—Lavender Green 000761 (HCC).

*Strength.*—Sturdy and upright.

Effect of Weather: This plant recommended only for greenhouse culture.

Persistance: Florets hang on and dry.

Lasting Quality: On plant—3 weeks; as cut flower—2 weeks.

same physiological and morphological characteristics as the parent.

The following is a color comparison of the new variety with its parent:

REPRODUCTIVE ORGANS

Stamens: Number—5.

*Arrangement.*—Syngenesious, connate by the anthers to form a cylinder about the style.

*Filaments.*—¼ inch long. Light Yellow in color.

*Pollen.*—Color—Yellow.

Pistils: Number—one for each ray floret.

*Styles.*—3/16 to ⅜ inch long.

*Stigmas.*—Color—Yellow.

Ovaries: Inferior and bicarpellate.

This new variety of chrysanthemum plant is particularly characterized by the improved color of its blooms which is deeper and more intense than that of the parent plant, the cultivar "Yellow Dignity". Otherwise and in all respects this new variety exhibits substantially the

| | Imp. Yel. Dignity | | Yellow Dignity | |
|---|---|---|---|---|
| | Summer | Winter | Summer | Winter |
| Outer florets, upper side | 4B | 6B | 4D | 4C |
| Outer florets, under side | 4C | 6C | 4D | 2D |
| Inner florets, upper side | 5A | 6A | 4B | 5C |
| Inner florets, under side | 5B | 6B | 4C | 4B |

I claim:

1. A new and distinct variety of chrysanthemum morifolium substantially as herein shown and described, characterized by the more intense yellow color if its blooms when compared to the cultivar "Yellow Dignity".

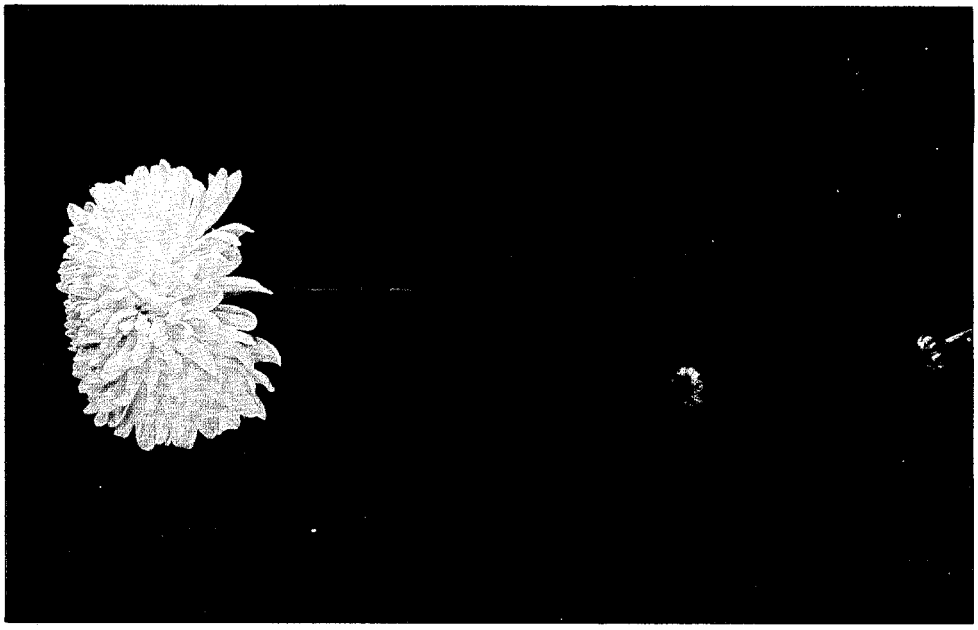
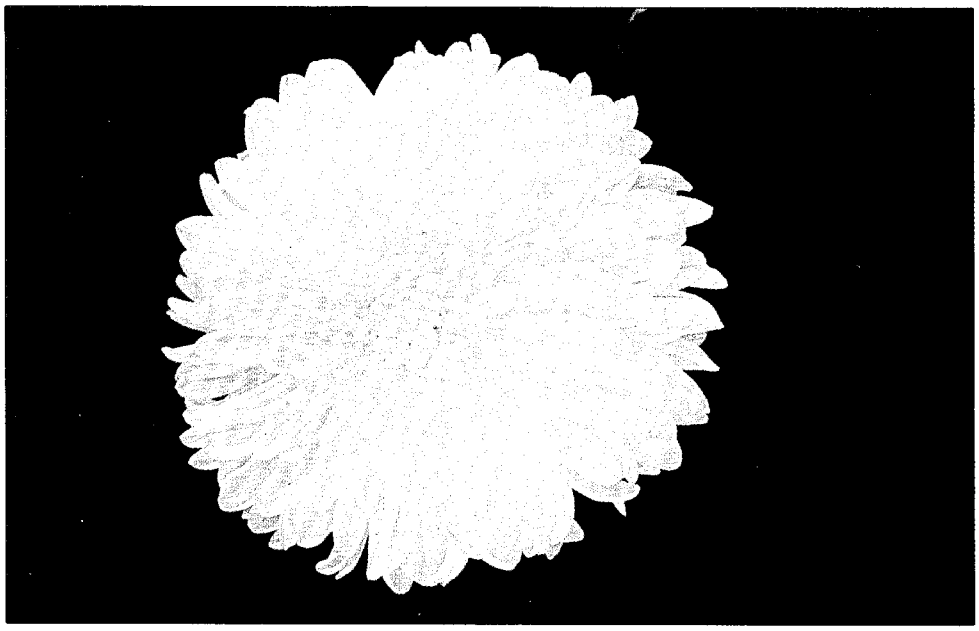

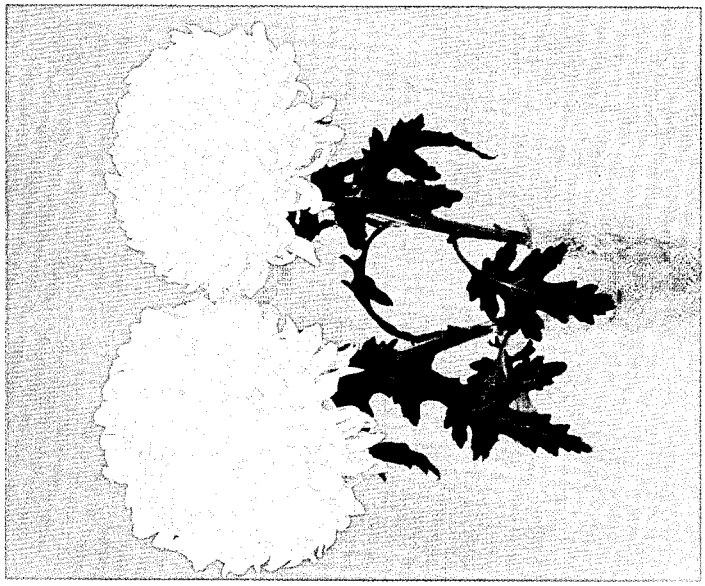
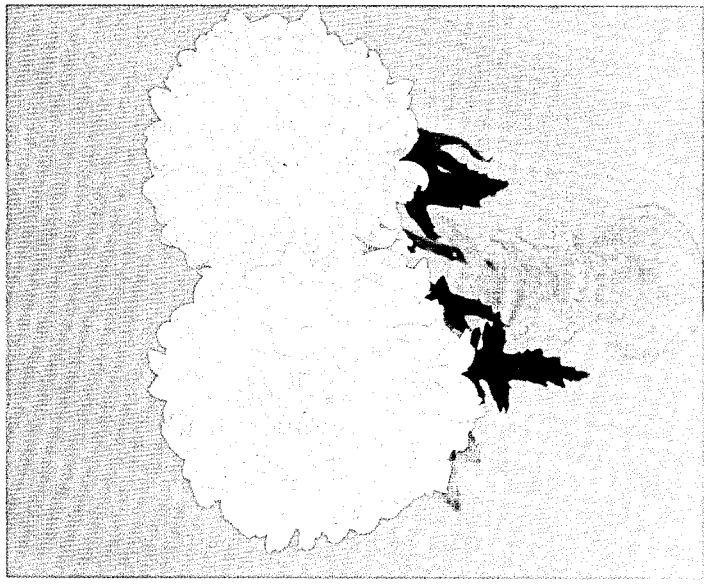

* * * * *